United States Patent

Powell et al.

[11] Patent Number: 5,906,595
[45] Date of Patent: May 25, 1999

[54] TROCAR HAVING PROTECTOR WITH FLEXIBLE END AND IMPROVED SEAL ASSEMBLY

[75] Inventors: Darrel M. Powell; Richard F. Schwemberger, both of Cincinnati; Salvatore Privitera, West Chester; William D. Kelly, Mason; David J. Keilholz, Cleves, all of Ohio

[73] Assignee: Ethicon Endo-Surgery, Inc., Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/846,221

[22] Filed: Apr. 25, 1997

[51] Int. Cl.$^6$ ..................................................... A61B 17/34
[52] U.S. Cl. ........................... 604/167; 606/185; 604/164
[58] Field of Search .................................. 604/167, 169, 604/164; 606/185

[56] References Cited

U.S. PATENT DOCUMENTS

| | | | |
|---|---|---|---|
| 3,118,468 | 1/1964 | Bochan | 137/525.1 |
| 3,313,299 | 4/1967 | Spademan | 128/214.4 |
| 3,585,996 | 6/1971 | Reynolds et al. | 128/214.4 |
| 3,861,416 | 1/1975 | Wichterle | 137/525.3 |
| 4,096,860 | 6/1978 | McLaughlin | 128/214.4 |
| 4,143,853 | 3/1979 | Abramson | 251/149.1 |
| 4,177,814 | 12/1979 | Knepshield et al. | 128/348 |
| 4,222,126 | 9/1980 | Boretos et al. | 3/1.5 |
| 4,261,357 | 4/1981 | Kontos | 128/214.4 |
| 4,364,127 | 12/1982 | Pierce et al. | 3/1.5 |
| 4,424,833 | 1/1984 | Spector et al. | 137/849 |
| 4,475,548 | 10/1984 | Muto | 128/207.14 |
| 4,535,773 | 8/1985 | Yoon | 604/51 |
| 4,540,411 | 9/1985 | Bodicky | 604/169 |
| 4,581,019 | 4/1986 | Curelaru et al. | 604/164 |
| 4,629,450 | 12/1986 | Suzuki et al. | 604/164 |
| 4,670,008 | 6/1987 | Von Albertini | 604/165 |
| 4,673,393 | 6/1987 | Suzuki et al. | 604/167 |
| 4,729,914 | 3/1988 | Kliment et al. | 428/36 |
| 4,772,264 | 9/1988 | Cragg | 604/158 |
| 4,798,594 | 1/1989 | Hillstead | 604/167 |
| 4,809,679 | 3/1989 | Shimonaka et al. | 128/4 |
| 4,862,891 | 9/1989 | Smith | 128/343 |
| 4,935,008 | 6/1990 | Lewis, Jr. | 604/52 |
| 4,950,257 | 8/1990 | Hibbs et al. | 604/265 |
| 4,954,130 | 9/1990 | Edwards | 604/169 |
| 4,978,334 | 12/1990 | Toye et al. | 604/51 |
| 4,981,482 | 1/1991 | Ichikawa | 606/108 |
| 4,994,027 | 2/1991 | Farrell | 604/53 |
| 5,009,643 | 4/1991 | Reich et al. | 604/165 |
| 5,030,206 | 7/1991 | Lander | 604/164 |
| 5,041,097 | 8/1991 | Johnson | 604/167 |
| 5,064,416 | 11/1991 | Newgard et al. | 604/167 |
| 5,066,288 | 11/1991 | Deniega et al. | 604/274 |
| 5,092,846 | 3/1992 | Nishijima et al. | 604/165 |
| 5,112,308 | 5/1992 | Olsen et al. | 604/164 |
| 5,141,498 | 8/1992 | Christian | 604/167 |
| 5,180,373 | 1/1993 | Green et al. | 604/167 |
| 5,197,955 | 3/1993 | Stephens et al. | 604/167 |
| 5,209,737 | 5/1993 | Ritchart et al. | 604/167 |
| 5,211,370 | 5/1993 | Powers | 251/4 |
| 5,211,653 | 5/1993 | Nakajima | 606/188 |
| 5,215,526 | 6/1993 | Deniega et al. | 604/164 |
| 5,224,952 | 7/1993 | Deniega et al. | 606/184 |
| 5,242,412 | 9/1993 | Blake, III | 604/167 |
| 5,248,298 | 9/1993 | Bedi et al. | 604/51 |
| 5,256,149 | 10/1993 | Banik et al. | 604/164 |
| 5,267,965 | 12/1993 | Deniega | 604/164 |
| 5,269,763 | 12/1993 | Boehmer et al. | 604/167 |
| 5,300,036 | 4/1994 | Mueller et al. | 604/167 |
| 5,314,417 | 5/1994 | Stephens et al. | 604/264 |
| 5,330,437 | 7/1994 | Durman | 604/167 |
| 5,354,280 | 10/1994 | Haber et al. | 604/167 |
| 5,360,417 | 11/1994 | Gravener et al. | 604/278 |
| 5,387,197 | 2/1995 | Smith et al. | 604/164 |
| 5,399,167 | 3/1995 | Deniega | 604/164 |
| 5,407,433 | 4/1995 | Loomas | 604/167 |
| 5,545,142 | 8/1996 | Stephens et al. | 604/167 |
| 5,549,565 | 8/1996 | Ryan et al. | 604/167 |
| 5,609,604 | 3/1997 | Schwemberger et al. | 606/185 |
| 5,697,913 | 12/1997 | Sierocuk et al. | 604/164 |
| 5,730,755 | 3/1998 | Yoon | 606/185 |

FOREIGN PATENT DOCUMENTS

| | | |
|---|---|---|
| 0267584 A2 | 5/1988 | European Pat. Off. . |
| 0316096 A2 | 5/1989 | European Pat. Off. . |
| 0336903 A1 | 10/1989 | European Pat. Off. . |

| 0426407 A2 | 5/1991 | European Pat. Off. . |
| 0510851 A1 | 10/1992 | European Pat. Off. . |
| 0647434 A2 | 4/1995 | European Pat. Off. . |
| 3737121 A1 | 5/1989 | Germany . |
| WO 93/04717 | 3/1993 | WIPO . |

*Primary Examiner*—Michael H. Thaler
*Attorney, Agent, or Firm*—Louis J. Capezzuro

[57] ABSTRACT

A surgical trocar has a cannula assembly including a sleeve having a proximal end, a distal end and a passageway therethrough. A housing having an opening is located at the proximal end of the sleeve and is aligned with the passageway of the sleeve. The trocar also includes an obturator assembly which is insertable in the cannula assembly. The obturator assembly includes a handle and an obturator shaft. The obturator shaft has a proximal end connected to the handle and a distal end opposite the proximal end. A penetrating tip is located at the shaft distal end for penetrating tissue. A protector having a distal end is slidably disposed around the obturator shaft for covering the penetrating tip. The protector has an aperture at its distal end for permitting the penetrating tip to pass therethrough. The protector also includes a flexible proximal end movable against the obturator handle to expose the penetrating tip when a proximal force is asserted against the protector. A seal assembly is located in the housing for sealing against the obturator assembly or surgical instruments passed through the cannula assembly. The seal assembly includes an upper seal arrangement having an aperture. The seal assembly also includes a pressure seal located beneath the upper seal arrangement. The pressure seal includes a pair of side walls. At least one rib is located on the inner surface of each side wall.

21 Claims, 7 Drawing Sheets

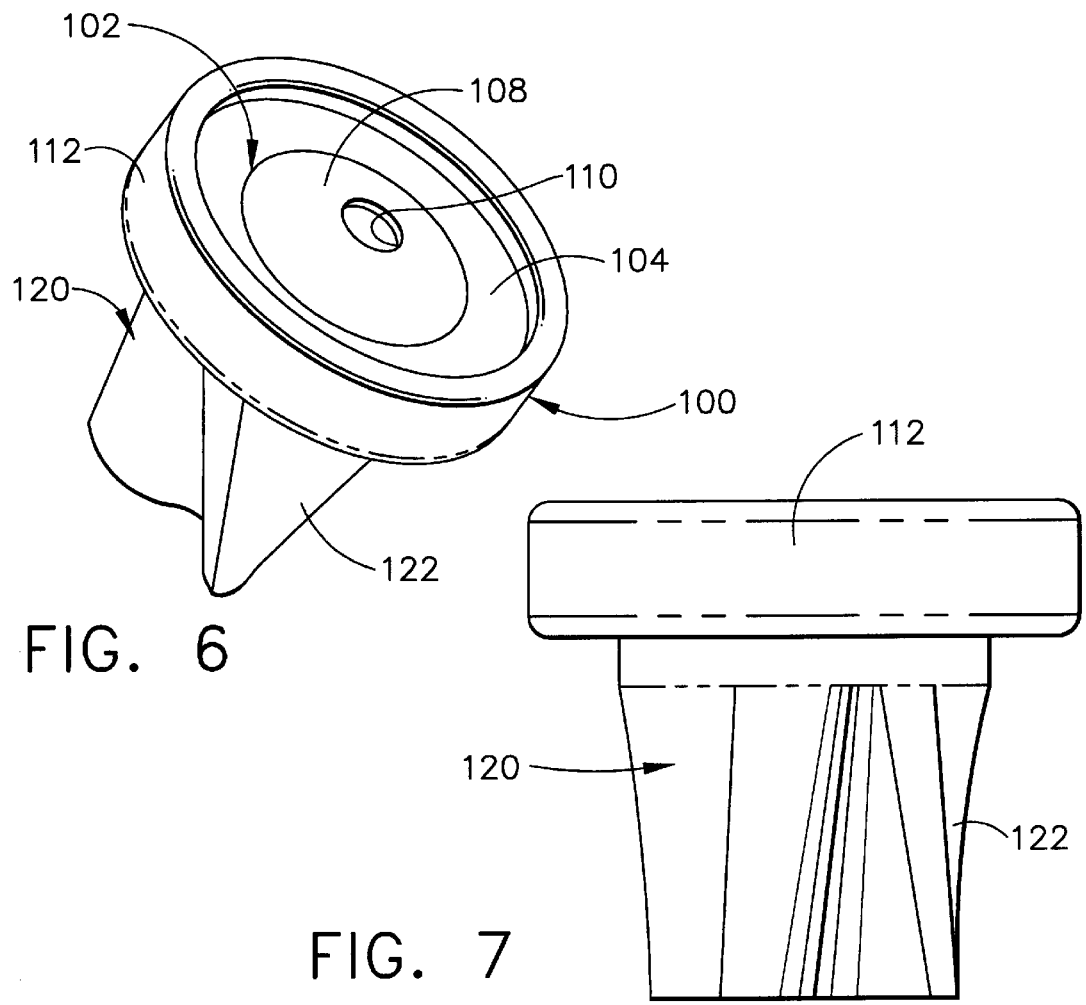
FIG. 6
FIG. 7
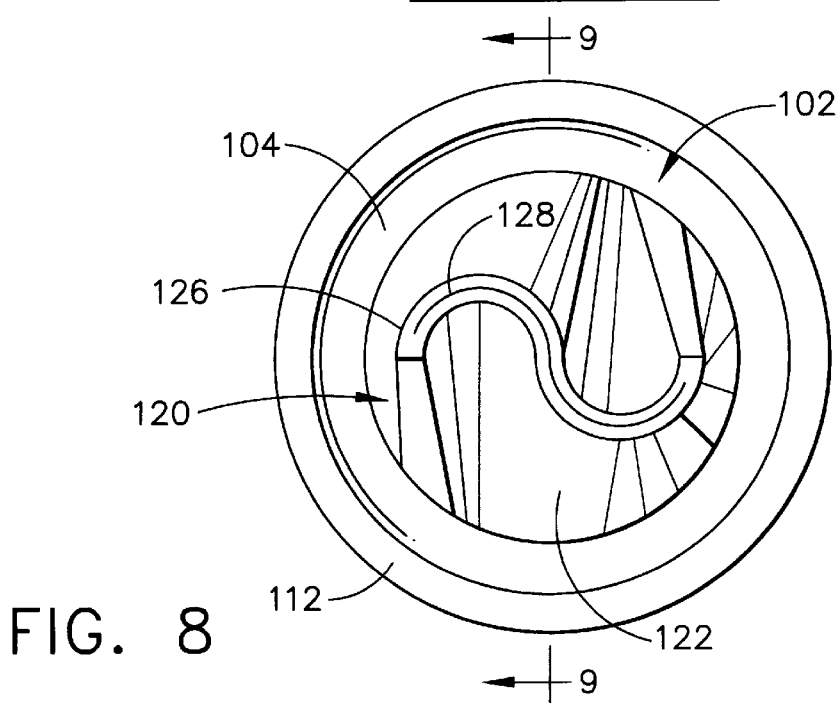
FIG. 8

TROCAR HAVING PROTECTOR WITH FLEXIBLE END AND IMPROVED SEAL ASSEMBLY

FIELD AND BACKGROUND OF THE INVENTION

The present invention relates in general to endoscopic surgery, and in particular, to trocars having shields or protectors for use in endoscopic surgical procedures.

The use of endoscopic procedures in surgery has become widely accepted. The term endoscopic as used herein is defined to include all types of minimally invasive surgical procedures including laparoscopic and arthroscopic procedures. Accordingly, numerous endoscopic instruments have been developed which allow the surgeon to perform complex surgical procedures with minimal incisions into the skin and tissue surrounding a particular body cavity or anatomical region. In order to introduce the endoscopic instrumentation into the body cavity, it is often necessary to puncture and cannulate the body cavity by using a trocar. Trocars are widely known in the art and typically consist of an obturator and a trocar cannula.

It is common for a sealing arrangement or sealing device to be used in association with the cannula to prevent the escape of fluid or gas during endoscopic procedures. During an endoscopic surgical procedure, the internal gas pressure must be maintained in order to successfully complete the procedure. In order to maintain the internal gas pressure while instruments are passed into and out of the trocars positioned in the abdominal cavity, sealing devices are required for both the instruments and for the trocar assemblies. It is desirable for such sealing devices to seal any opening within the trocar assembly when the obturator is withdrawn after puncturing the abdominal wall. It is also desirable to seal when other surgical instruments are inserted through the trocar cannula throughout the remainder of the surgical procedure. Furthermore, it is desirable that the sealing device maintain gas pressure in the abdominal cavity, despite numerous insertions and withdrawals of surgical instruments through the trocar cannula.

Current sealing devices for endoscopic instruments are typified by particular valve designs such as that described in U.S. Pat. No. 5,224,952 (Deniega et al.). This design includes a spring loaded valve in combination with a sealing gasket to conform to the cross section of the surgical instrument inserted through the trocar. This two part valve assembly performs adequately as a seal but may be more complex than truly desired. U.S. Pat. No. 5,141,498 (Christian) shows at least three flexible leaflets, and U.S. Pat. No. 4,424,833 (Spector et al.) shows a sponge type valve with three connecting slits. Multiple leaflet and multiple slit valves may seal well when a surgical instrument is not inserted through them but will tend to create gaps around inserted instruments having circular cross sections and will also tend to cause inversion of their sealing surfaces when the instruments are withdrawn. Inversion of the sealing surfaces is likely to cause gaps between the sealing surfaces resulting in gas leakage through the seal. U.S. Pat. No. 5,242,412 (Blake) shows a duck bill valve design applied to a trocar device. This design provides a straight single slit to seal against a surgical instrument. U.S. Pat. Nos. 4,475,548 (Muto); 4,809,679 (Shimonaka et al.); and 4,143,853 (Abramson) show single slit designs also. A single slit valve is also subject to a lack of conforming to circular cross-section shapes and to inversion upon withdrawal of surgical instruments.

Variations of the single slit design are shown in U.S. Pat. Nos. 4,798,594 (Hillstead); 4,177,814 (Knepshield et al.); and 4,673,393 (Suzuki et al.). The variations shown in these patents encompass three slits radiating from the seal center and possess similar characteristics as the single slit regarding sealing around circular instruments and eversion. Other surgical valves include specialized designs typified by heart valves shown in U.S. Pat. Nos. 4,364,127 (Pierce et al.); 3,861,416 (Wichterle); and 4,222,126 (Boretos et al.). These valves are designed to allow one direction flow of heavy liquids and include at least three flaps. Such valves are not intended to seal around surgical instruments against loss of gas pressure.

A study of these references indicates a need for a simpler one piece assembly for use in trocars to seal against gas pressure during endoscopic surgical procedures. In addition, it is desirable to have a one piece assembly with a simple design which would not require an excessive force to insert an instrument through it and would resist inversion of the sealing edges once the surgical instrument is withdrawn.

One known seal assembly design which has been developed in an attempt to solve the sealing needs outlined above is disclosed in U.S. Pat. No. 5,330,437 (Durman) which is incorporated herein by reference. This seal assembly design includes a one piece assembly having a duck bill valve in a S-shaped configuration. Although this particular seal design has proved to be successful in addressing some of the drawbacks found in the other known sealing devices, as will be shown later in this disclosure, this seal design can be improved in order to significantly reduce forces to insert and extract surgical instruments.

Additionally, trocars may have a protective element around the obturator which covers the sharp piercing tip of the obturator prior to and after insertion, and also after removal of the obturator and trocar cannula. The protective element is often referred to as a safety shield or protector.

One type of trocar utilizes a safety shield and is typically inserted by pressing the distal end of the trocar assembly against the outer skin of the patient with sufficient force to cause the piercing end of the obturator to pierce through the skin, underlying fat, muscle and fascia into the body cavity. The trocar is permitted to penetrate into the body cavity because the safety shield is retracted proximally thereby exposing the sharp piercing tip. However, upon completing the penetration, the safety shield automatically returns to its protective position covering the piercing tip. This type of trocar is a fully returnable safety shielded trocar. Once the surgeon has properly positioned the trocar within the body cavity, the obturator together with the safety shield are removed and the trocar cannula is then available as a pathway, e.g., for insertion of endoscopic instrumentation. U.S. Pat. No. 5,387,197 (Smith et al.) describes this type of trocar.

With current fully returnable safety shielded trocars, it may be necessary to remove the cannula handle from the obturator handle to "reload" the shield on the trocar obturator for those instances where the trocar has not completely penetrated into the body cavity. In this fashion, therefore, it is necessary to perform an extra step while the obturator tip is inserted within pneuoperitoneum.

Yet, in some procedures it may be desirable to utilize trocars without a safety shield or to utilize a trocar design wherein the trocar obturator is nonshielded at the time when the trocar obturator is placed within the trocar cannula. Thus, upon coupling of the shielded obturator and the cannula, the shield will be retracted thereby exposing the piercing tip of the obturator. This type of trocar can be referred to as an assembly actuated trocar.

An assembly actuated trocar prevents the shield from returning to its protective position upon placement of the obturator within the cannula. U.S. Pat. No. 5,248,298 (Bedi et al.) describes this type of trocar. In this way, the user is able to slightly withdraw the trocar from the pierced tissue, and then continue penetrating through remaining tissue layers. This prevents what is commonly referred to as "tenting" of pneumoperitoneum. In this fashion, tenting can be reduced while still adequately providing access to the body cavity.

In an effort to eliminate problems with tenting or to reduce cost from surgery, surgeons often utilize trocars that do not employ a safety shield since these types of trocars are generally less expensive than fully returnable safety shielded trocars. However, for those procedures that utilize trocars without a safety shield, there is a possibility that the obturator tip could cut a person handling the trocar or damage the trocar seal assembly or other components of the instrument.

Presently, there is no known trocar that provides a low cost option to the surgeon while maintaining the ability to protect the obturator piercing tip with a shield or protector up until the time when the obturator is coupled to the proximal end of the cannula.

Moreover, there is no known trocar that utilizes a seal assembly that significantly reduces the amount of force required to insert and extract surgical instruments.

SUMMARY OF THE INVENTION

The present invention is a surgical trocar for use in endoscopic surgical procedures such as minimally invasive procedures, laparoscopic procedures, arthroscopic procedures or the like.

The surgical trocar according to the present invention comprises a cannula assembly including a sleeve having a proximal end, a distal end and a passageway therethrough. A housing having an opening is located at the proximal end of the sleeve and is aligned with the passageway of the sleeve. The trocar also includes an obturator assembly which is engagable with the cannula assembly. The obturator assembly includes a handle and an obturator shaft. The obturator shaft has a proximal end connected to the handle and a distal end opposite the proximal end. A penetrating tip is located at the distal end of the obturator shaft.

The obturator assembly also includes a protector slidably disposed around the obturator shaft for covering the obturator penetrating tip. The protector has an aperture at a distal end of the protector for permitting the penetrating tip of the obturator shaft to pass therethrough. The protector also includes a flexible proximal end which is slidably movable against a contact portion of the handle for exposing the penetrating tip past the protector aperture and the sleeve distal end when the handle comes in contact with the housing upon the insertion of the obturator assembly into the cannula assembly. Thus, upon inserting the obturator assembly into the cannula assembly, a proximal force is applied to the protector which moves the protector proximally such that the flexible proximal end of the protector slidably moves against the contact portion of the handle. This contact causes the flexible proximal end to flex or deflect as the flexible proximal end is slidably moved against the contact portion of the handle.

According to the present invention, there are several embodiments for the flexible proximal end of the protector. One embodiment includes a pair of deflectable arms. A second embodiment for the flexible proximal end of the protector includes a sinusoidal member integral with the protector.

Another alternative embodiment according to the present invention provides a surgical trocar, and more particularly, an obturator assembly comprising a handle having an opening therein and a flexible engagement portion. The obturator shaft extends through the handle opening and has a proximal end fixed to the handle and a distal end with a penetrating tip thereon. A protector is slidably disposed around the obturator shaft and extends through the handle opening for covering the penetrating tip of the obturator shaft. The protector has an aperture at a distal end thereof which permits the penetrating tip of the obturator shaft to pass therethrough. The protector also has a proximal end which is slidably movable against the flexible engagement portion of the handle in order to retract the protector to a retracted position for exposing the penetrating tip when a proximal force is placed against the protector.

The present invention also provides for an improved seal assembly for a surgical trocar for sealing against a trocar obturator assembly or other surgical instruments. The seal assembly includes an upper seal arrangement having an aperture therethrough and a pressure seal beneath the upper seal arrangement. The pressure seal includes a pair of side walls wherein each side wall has an inner surface. At least one rib is located on the inner surface of each side wall. Each side wall is collapsible against the other and defines an S-shaped slit therebetween. The side wall ribs significantly reduce insertion and extraction forces for the obturator assembly or other surgical instruments. Additionally, the ribs also provide stiffening for the pressure seal to prevent inversion of the side walls when the obturator assembly or other surgical instruments are withdrawn through the seal assembly.

One advantage of the present invention is to provide a surgical trocar that provides protection for the surgeon or others all the way up until the moment that the obturator assembly is engaged with the cannula assembly.

Another advantage according to the present invention is to provide a surgical trocar that provides protection for the trocar seal and other components of the trocar.

Another advantage of the present invention is to provide a surgical trocar that eliminates tenting of the peritoneum.

It is another advantage of the present invention to provide a surgical trocar having an obturator protector to be used as a secondary port for endoscopic surgical procedures.

Another advantage of the present invention is to provide a seal assembly that permits a surgical instrument to be passed therethrough and significantly reduces the insertion and extraction forces typically associated with known sealing devices.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 6 is a perspective view of an improved seal assembly according to the present invention employed in the cannula of FIG. 5;

FIG. 7 is a side elevational view of the improved seal assembly shown in FIG. 6;

FIG. 8 is a front elevational view of the improved seal assembly shown in FIG. 6;

DESCRIPTION OF THE PREFERRED EMBODIMENTS

Figure 1:
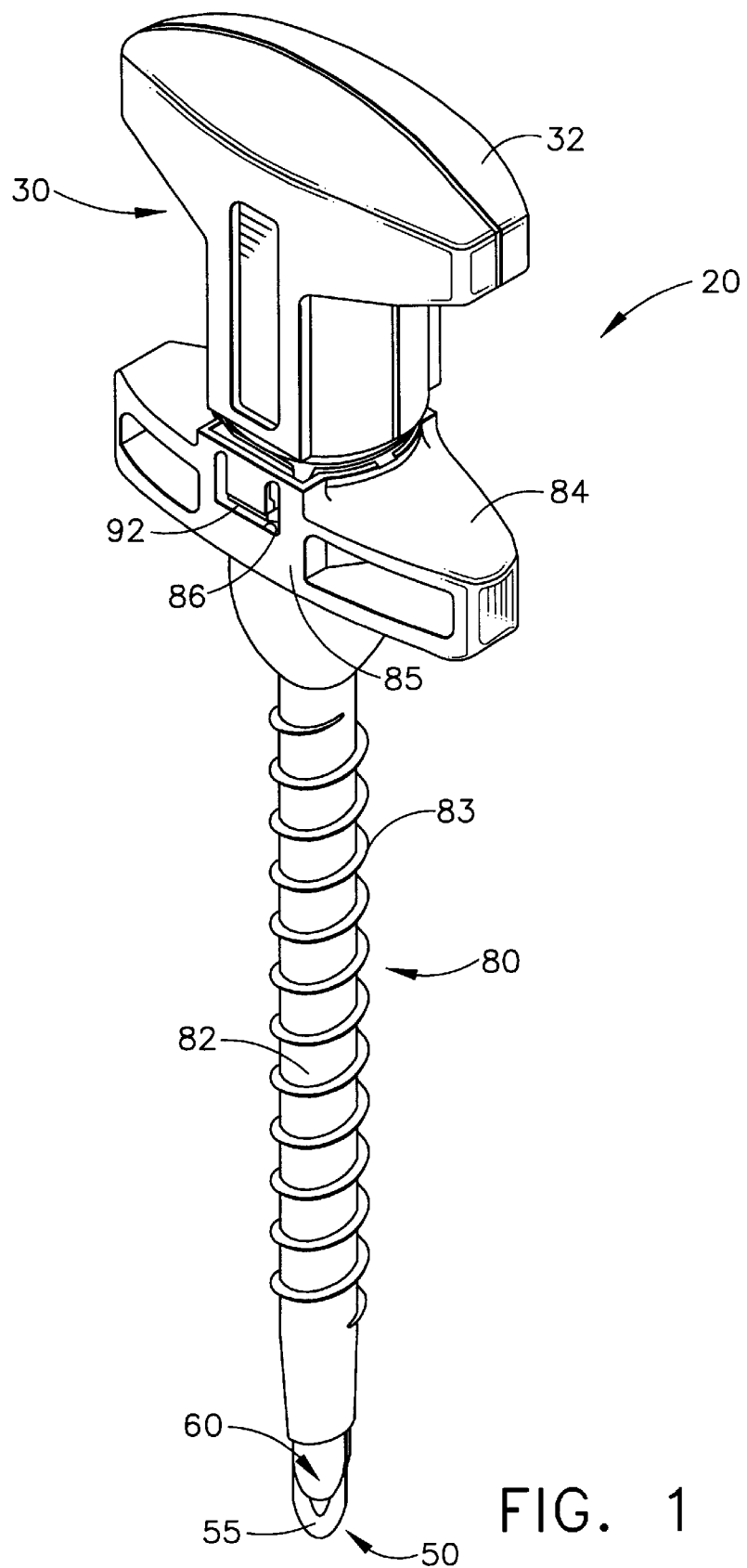
FIG. 1 is a perspective view of a trocar having an obturator and a cannula according to the present invention.

As best shown in FIG. 1, the present invention is a low cost surgical trocar, generally designated 20, utilized as an assembly actuated trocar for endoscopic surgical procedures to include all minimally invasive surgical procedures such as laparoscopic and arthroscopic surgical procedures. The surgical trocar 20 is disposable and is intended to be used as a single patient use only device, meaning that the trocar 20 according to the present invention is to be used on only one patient for a particular surgical procedure and then after such usage, the trocar 20 is to be discarded.

The surgical trocar 20 is similar to the trocars found in U.S. patent application Ser. Nos. 08/543,455 (Oct. 16, 1995); 08/543,547 (Oct. 16 1995); 08/572,172 (Dec. 13, 1995); 08/694,980 (Aug. 9, 1996) and U.S. Pat. Nos. 4,535,773; 5,224,952; 5,256,149; 5,314,417; 5,387,197; 5,248,298; 5,330,437; 5,399,167; 5,066,288; 5,215,526 and 5,267,965 all of which are incorporated herein by reference.

Figure 2:
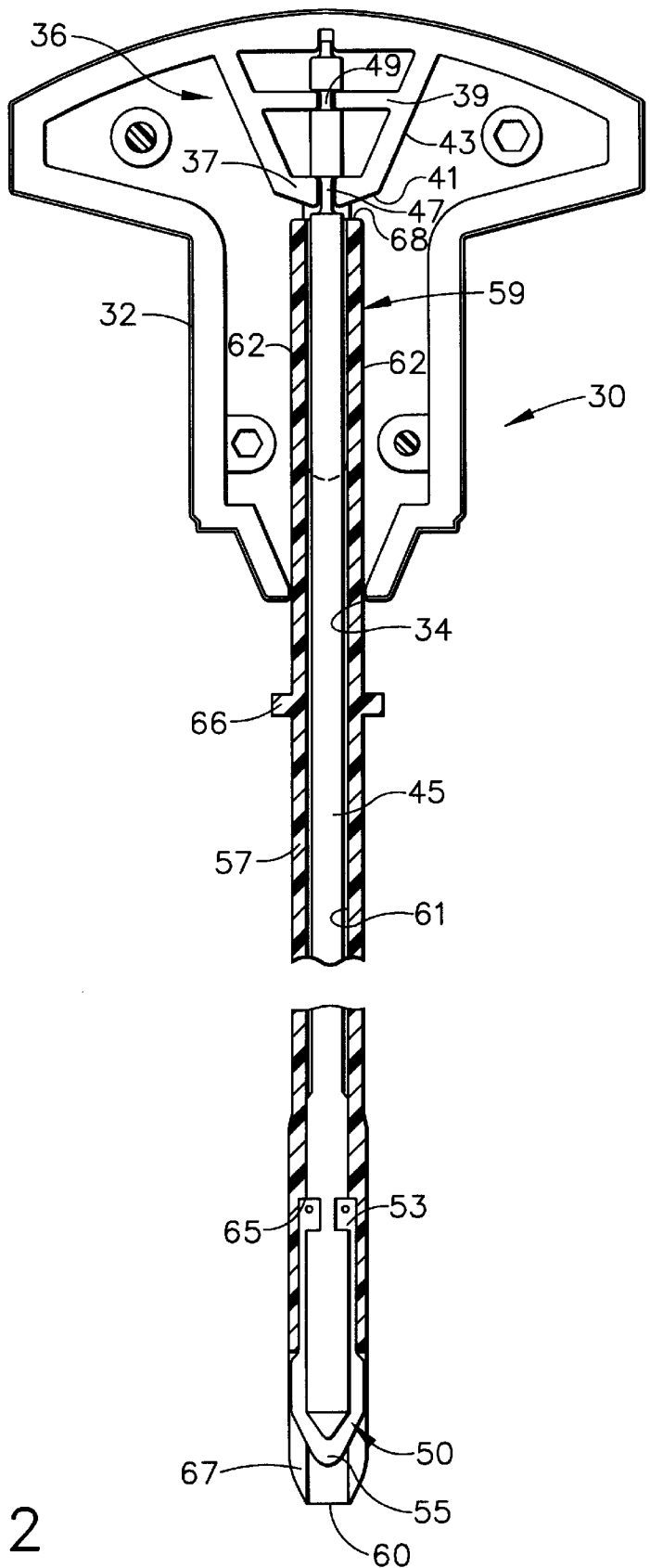
FIG. 2 is a plan view in section of the trocar obturator with a penetrating tip in a covered position according to the present invention.

The surgical trocar 20 includes an obturator assembly, generally designated 30, which is insertable through a cannula assembly, generally designated 80, for establishing a surgical access port. FIG. 2 shows the obturator assembly 30 comprising a handle 32 having an opening 34 at a lower portion of the handle 32. The handle 32 also includes a contact portion, generally designated 36, having a pair of first retaining ribs 37 and a pair of second retaining ribs 39 positioned proximally to the pair of first retaining ribs 37. Additionally, the contact portion 36 also includes a first ramp surface 41 and a second ramp surface 43 positioned at an obtuse angle to the first ramp surface 41.

An obturator shaft 45 having a first retained portion 47 and a second retained portion 49 at a proximal end of the obturator shaft 45 are fixedly secured to the handle 32 at the first retaining ribs 37 and the second retaining ribs 39 respectively. The remainder of the obturator shaft 45 extends from the handle 32 through the handle opening 34.

The obturator shaft 45 also includes a penetrating tip, generally designated 50, which is a blade assembly comprising a flat blade 55 for penetrating tissue and a pair of upper shoulders 53. The penetrating tip 50 is fixed to the distal end of the obturator shaft 45.

Figure 4:
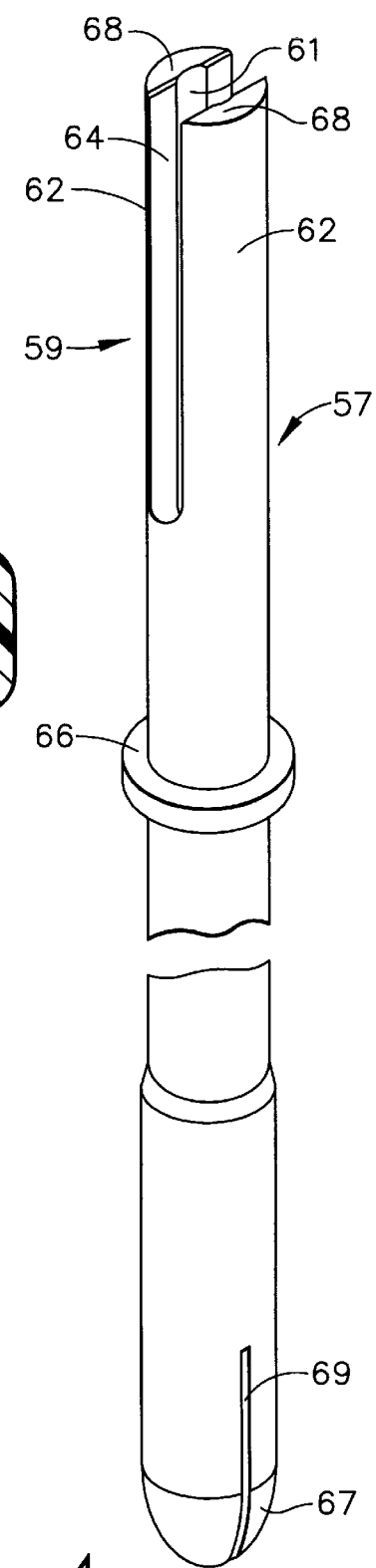
FIG. 4 is a perspective view, partially broken away, illustrating a protector according to the present invention.

A protector sleeve 57 having a channel 61 therethrough is slidably disposed around the obturator shaft 45. The protector 57 also includes a flexible proximal end 59 which is located, along with the proximal portion of the obturator shaft 45, within the handle 32. As shown in FIG. 4, the protector 57 is a single piece of molded plastic. The protector proximal end 59 includes a pair of deflectable arms 62 that are resilient and flexible enough so that the deflectable arms 62 can be deflected outwardly from the obturator shaft 45, but yet resume their original shape and size after deflection without breaking away from the protector 57. However, it is not intended that the protector 57 be limited merely to molded plastic, but can also include any type of material that contains the required properties and characteristics for the flexible proximal end 59 such as described above.

The protector deflectable arms 62 include an inner surface 64 and an end surface 68 at the end portion of each deflectable arm 62 as shown in FIG. 4. The end surfaces 68 of the protector deflectable arms 62 are initially located distally from the first ramp surfaces 41 of the handle contact portion 36 thus defining a gap between the first ramp surfaces 41 and the deflectable arm end surfaces 68.

Similar to the obturator shaft 45, the protector 57 extends from the handle 32 through the handle opening 34. The protector 57 also includes a dilating tip section 67 located at the distal end of the protector 57 for dilating tissue after the trocar 20 is inserted into tissue for establishing a surgical access port.

The protector 57 also includes a boss 66 circumferentially arranged around the exterior of the protector 57 and positioned near the handle opening 34. The dilating tip section 67 of the protector 57 includes an aperture 60 which communicates with the channel 61 of the protector 57. The aperture 60 is located at the distal end of the protector 57 for permitting the penetrating tip 50 of the obturator shaft 45 to pass therethrough.

The dilator tip 67 also includes a slot 69 which vertically extends from the aperture 60 to a point near the distal end of the protector 57 for permitting the penetrating tip 50 to pass therethrough (FIG. 4). The protector 57 also includes a stop 65 circumferentially arranged within the channel 61 at the dilator tip 67 for being supported by with the upper shoulders 53 of the penetrating tip 50.

Since, the flexible proximal end 62 of the protector 57 is located near the contact portion 36 within the handle 32, the protector 57 is slideably movable around the obturator shaft 45 between the upper shoulders 53 of the penetrating tip 50 of the obturator shaft 45 and the handle contact portion 36. The stop 65 is supported by the upper shoulders 53 of the penetrating tip 50 for preventing the protector 57 from disengaging from the obturator handle 32.

As best illustrated in FIG. 2, the obturator assembly 30 is in a protected position meaning that the protector 57 is extended beyond the penetrating tip 50 thereby covering the penetrating tip 50 and preventing any inadvertent cutting by the flat blade 55.

Figure 5:
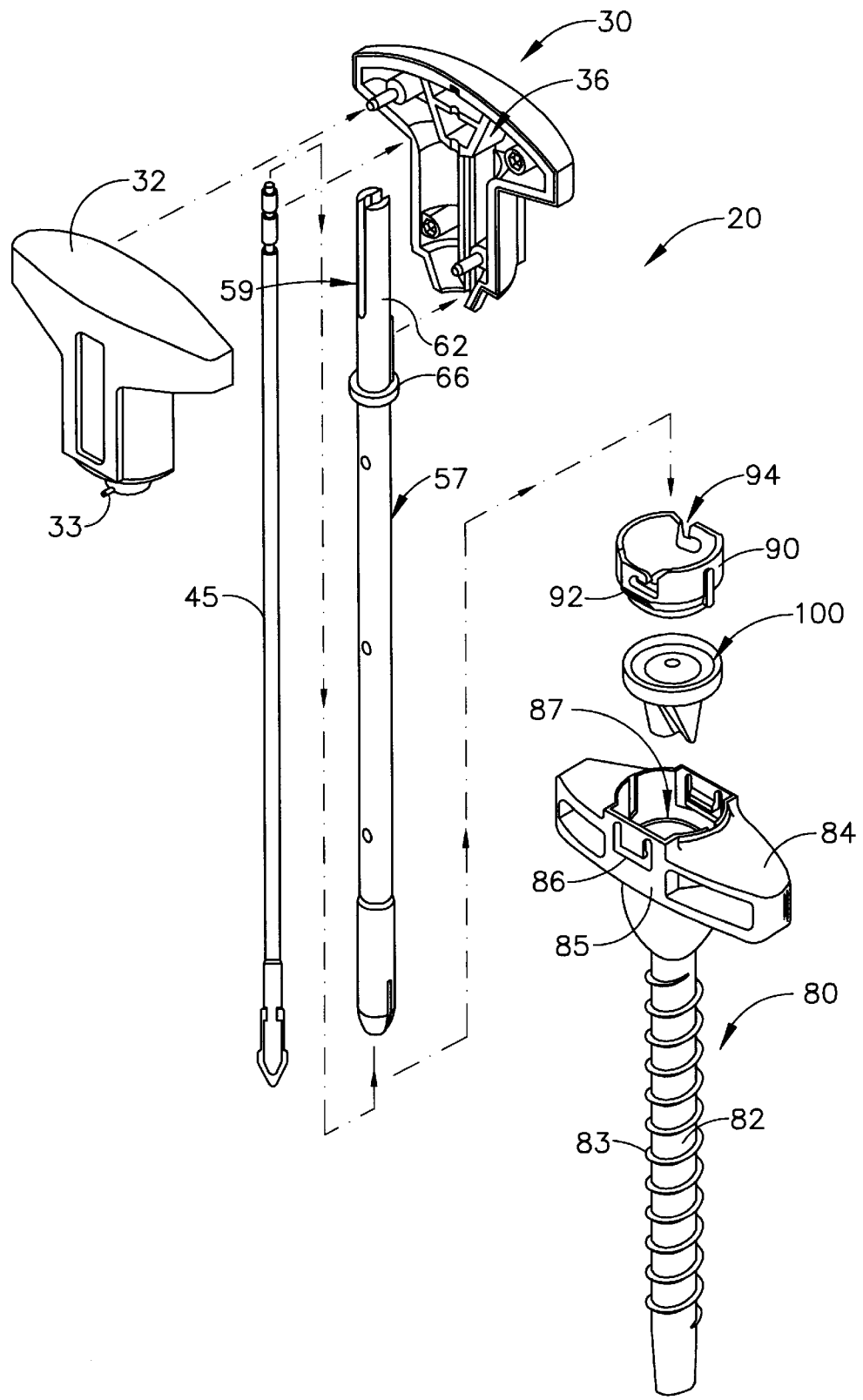
FIG. 5 is an exploded perspective view of the obturator and the cannula of FIG. 1.

FIG. 5 shows the cannula assembly 80 comprising a cannula sleeve 82 defining a central passageway therethrough and a seal housing 85 located at the proximal end of the sleeve 82. The sleeve 82 has a helical thread 83 on an exterior surface of the sleeve 82 for positioning the sleeve 82 in tissue. The housing 85 also includes a handle portion 84 which extends outwardly and substantially perpendicular from opposite sides of the housing 85. The housing 85 includes a central opening 87 for receiving a seal assembly, generally designated 100, therein. The seal assembly 100 is disposed in the central opening 87 and is seated above the cannula sleeve 82. The housing 85 also includes a seal retainer 90 having two retainer locks 92 and is seated against the upper surface of the seal assembly 100 and fixed to the cannula housing 85. The seal retainer 90 is a conical plastic ring which permits the obturator assembly 30 to be inserted directly through the seal assembly 100.

The housing 85 also includes a pair of retainer lock slots 86 located on opposite sides of the housing 85 for receiving the retainer locks 92 of the seal retainer 90. Accordingly, the retainer locks 92 of the retainer 90 are pressed fit into the retainer lock slots 86 of the housing 85 as best illustrated in FIG. 1.

Figure 3:
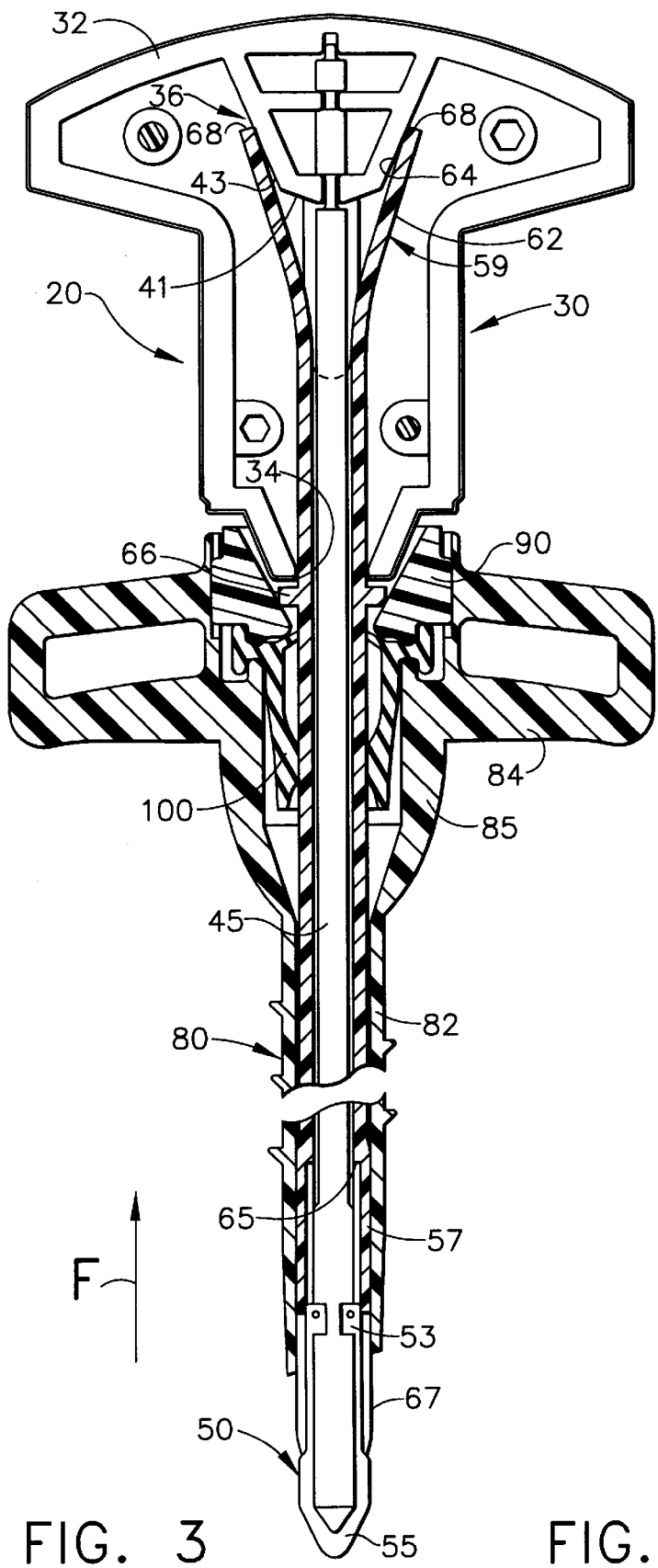
FIG. 3 is a plan view in section of the obturator of FIG. 2 in a coupled relationship with the cannula of FIG. 1 with the penetrating tip in an exposed position.

As best illustrated in FIG. 3, the penetrating tip 50 is exposed by retracting the protector 57 to a retracted position proximally within the cannula handle 32. Upon a proximal force F being asserted against the protector 57, the deflectable arm end surfaces 68 contact the first ramp surfaces 41 of the handle contact portion 36 and are slidably movable across the first ramp surfaces 41 of the handle contact portion 36. After initial contact of the end surfaces 68 with the first ramp surfaces 41, the deflectable arms 62 are deflected outwardly away from the obturator shaft 45 as the protector 57 is forced proximally within the handle 32 through the application of proximal force F since the deflectable arms 62 are made of a resilient, flexible material. Due the material properties of the proximal end 59, an opposing force is applied to the protector 57 as the deflectable arms 62 are slidably moved against the contact portion 36. These material properties cause the protector 57 to return distally to a protected position when the proximal force F is released from the protector 57.

Once the deflectable arm end surfaces 68 are slid past the first ramp surfaces 41, the inner surfaces 64 of the deflectable arms 62 contact the second ramp surfaces 43 of the handle contact portion 36 and are slidably movable across the second ramp surfaces 43. Accordingly, the end surfaces 68 and the inner surfaces 64 of the deflectable arm 62 are slideably movable against the first ramp surfaces 41 and the second ramp surfaces 43 of the handle contact portion 36 respectively to facilitate a smooth retraction of the protector 57 within the obturator handle 32. The first ramp surfaces 41 are arranged substantially perpendicular to the obturator shaft 45 in order to provide a sufficient resistive surface for the deflectable arms 62 to prevent the deflectable arms 62 from easily sliding past the first ramp surfaces 41. This arrangement ensures that the protector 57 is not inadvertently withdrawn into the obturator handle 32 until intended. Because the second ramp surfaces 43 are at an obtuse angle with respect to the first ramp surfaces 41, there is a less resistive surface for the deflectable arms 62. This allows the protector 57 to be easily retracted at this point in the retraction.

The protector is retracted to its retracted position through the application of the proximal force F which can be applied to the protector 57 manually, for instance, by the surgeon grasping the protector boss 66 and withdrawing the protector 57 proximally toward the handle 32. Alternatively, the protector 57 is retracted to its retracted position upon insertion of the obturator assembly 30 through the cannula assembly 80 and into the cannula sleeve 82 until the dilator tip 67 of the protector 57 extends through the distal end of the cannula sleeve 82 as shown in FIGS. 1 and 3 and up until the point where the protector boss 66 contacts the handle 32 at the handle opening 34. At this point, the boss 66 of the protector 57 will contact the inner surface of the conically-shaped retainer 90 thereby causing the proximal force F to be asserted against the protector 57. The proximal force F advances the protector 57 proximally within the handle 32 for extending the penetrating tip 50 through the protector aperture 60 thereby exposing the flat blade 55 for cutting tissue. The handle opening 34 has a smaller diameter than the outer diameter of the circumferentially arranged protector boss 66 such that the protector boss 66 cannot be inserted within the obturator handle 32.

Additionally, as shown in FIG. 5, the obturator handle 32 also includes retaining pins 33 laterally extending from the handle adjacent the handle opening 34. Thus, the obturator assembly 30 can be locked to the cannula assembly 80 by rotating the retaining pins 33 into the pin slots 94 of the seal retainer 90 through a slight rotation motion of the handle 32 once the obturator assembly 30 has been inserted through the cannula assembly 80 thereby forming the assembly actuated trocar 20.

The handle 32 is unlocked merely through reversing the rotation action such that the rotating pins 33 disengage from the pin slots 94 which will cause the protector 57 to return to its protected position covering the penetrating tip 50. The resilient, flexible properties of the protector proximal end 59 will cause the protector 57 to advance distally over the penetrating tip 50 upon the decoupling of the handle 32 from the cannula housing 85.

As shown in FIGS. 6–10, the seal assembly 100 is made of a silicone material and includes a housing seal 104 which is a circumferential elastomeric member that surrounds a diaphragm seal 108. The diaphragm seal has a central aperture 110 therethrough and has a substantially convex shape which extends upwardly and outwardly from the housing seal 104. Both the housing seal 104 and the diaphragm seal 108 form an upper seal arrangement, generally designated 102, for the seal assembly 100. A flange 112 surrounds the outer periphery of the housing seal 104.

Additionally, the seal assembly 100 also includes an S-shaped pressure seal 120 comprising two sidewalls 122 extending distally from the under side of the housing seal 104 and the diaphragm seal 108. As shown in FIG. 8, each sidewall 122 is collapsible against each other and each sidewall 122 has an end section 126 that is adjacent to each other and define an S-shaped slit 128 therebetween. Accordingly, the central aperture 110 and the S-shaped slit 128 of the seal assembly 100 permit the obturator assembly 30 (FIG. 2) to be inserted therethrough in sealing engagement thereby preventing the loss of operating fluid. However, once the cannula assembly 80 (FIG. 5) has been placed, the obturator assembly 30 can be withdrawn from the cannula assembly 80 for the insertion of additional surgical instruments through the cannula assembly 80 for facilitating the surgical procedure. Similar to obturator assembly 30, additional surgical instruments inserted through the seal assembly 100 are sealed by the seal assembly 100, particularly by the S-shaped pressure seal 120 and the upper seal arrangement 102.

Figure 9:
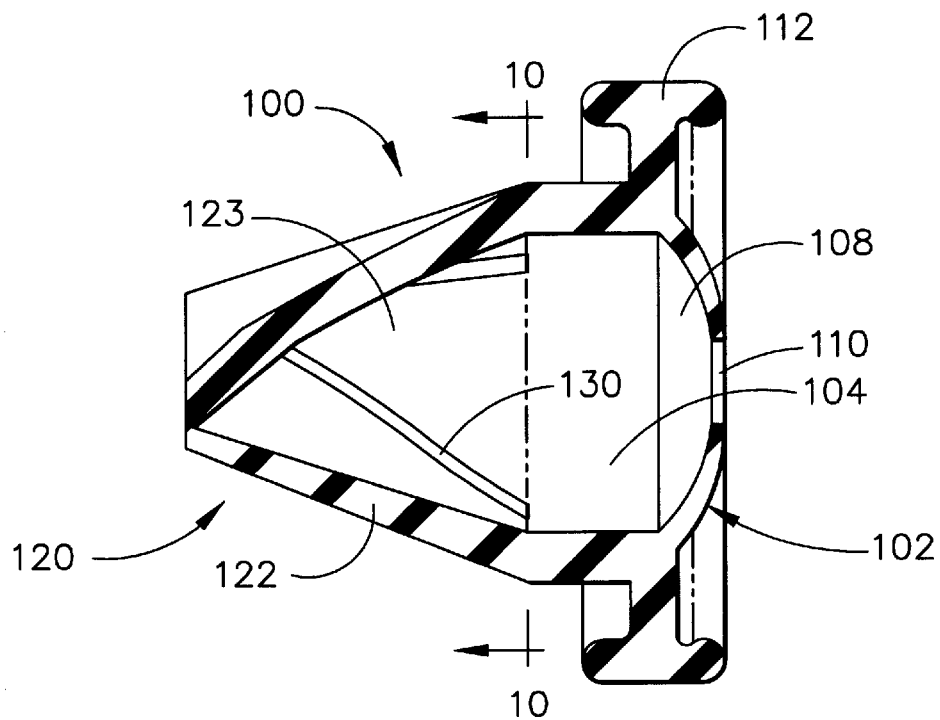
FIG. 9 is a longitudinal section view of the improved seal assembly shown in FIG. 6 taken along Line 9—9 of FIG. 8.
Figure 10:
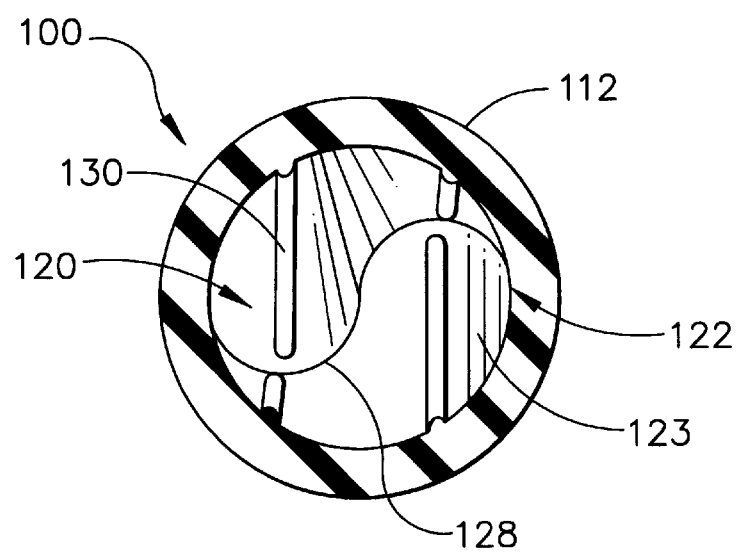
FIG. 10 is a lateral section view of the improved seal assembly taken along Line 10—10 of FIG. 9.

As shown in FIGS. 9 and 10, each side wall 122 includes an inner surface 123. A plurality of ribs 130 are located on the inner surface 123 of each side wall 122. The ribs 130 extend distally from the proximal portion of the pressure seal 120 to the slit 128. The ribs 130 provide stiffening for the side walls 122 which help prevent and resist inversion of the side walls 122 once the obturator assembly 30 (FIG. 2) or other surgical instruments are withdrawn from the seal assembly 100 after use.

Without the ribs 130, the seal assembly 100 would have a tendency for instruments to adhere to the inner surface 123 of the side walls 122 which increases friction for any instruments inserted therethrough since the seal assembly 100 is generally made from silicone.

Therefore, through the inclusion of the side wall ribs 130 on the side wall inner surfaces 123, the side wall ribs 130 reduce the contact area for the obturator assembly 30 (FIG. 2) or any other surgical instrument, and accordingly, significantly lower the frictional forces caused be either the insertion or withdrawal of the obturator assembly 30 or other surgical instruments.

In side-by-side comparison testing, the seal assembly 100 according to the present invention was found to be far superior in performance to the prior art seal disclosed in U.S. Pat. No. 5,330,437 (Durman) which does not utilize ribs. A test was conducted that utilized both the Durman seal and the present invention seal assembly 100. Both the Durman seal and the present invention seal assembly 100 were tested for required insertion and extraction forces utilizing a probe under the same conditions in a post-heat aging environment. For the Durman seal, there was a 0.32 lb. force required to insert the probe and a 0.46 lb. force requirement to extract the probe. However, for the present invention seal assembly 100, there was a 0.20 lb. force requirement to insert the probe and a 0.20 lb. force requirement to extract the probe. Accordingly, the ribs 130 of the present invention seal assembly 100 accounted for the drastic reduction in both insertion and extraction forces when compared to the Durman seal.

Figure 12:
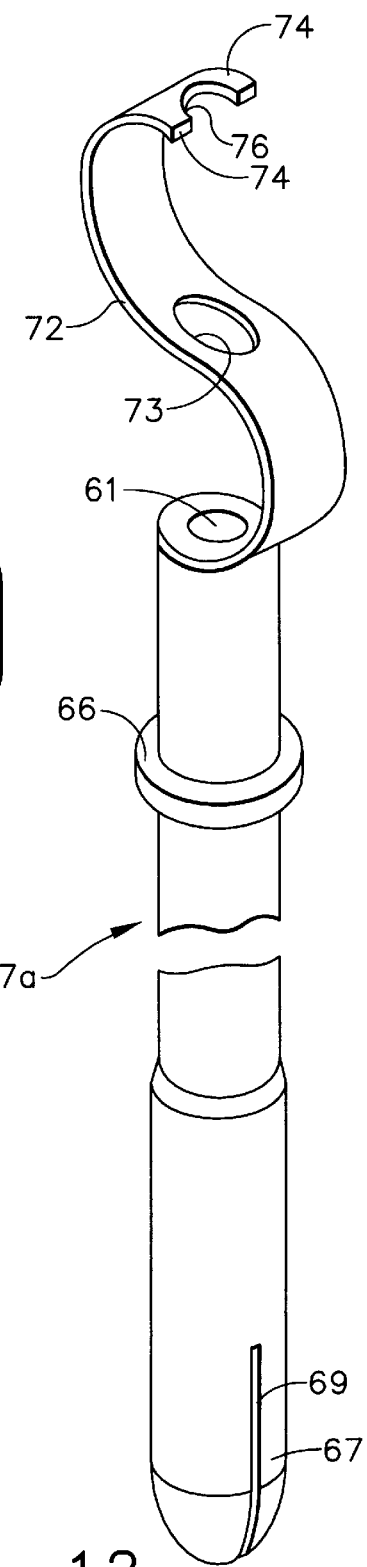
FIG. 12 is an alternate embodiment of the protector of FIG. 3.

A second embodiment of a protector 57a according to the present invention is illustrated in FIG. 12 wherein the protector 57a includes a flexible proximal end 59a which is a sinusoidal member 72 having a central bore 73 and a pair of proximal tips 74 having a notch 76 interposed between each tip 74. The notch 76 and the central bore 73 are aligned directly with the channel 61 of the protector 57a. Both the notch 76, the central bore 73, along with the channel 61 of the protector 57a are shaped to receive the obturator shaft 45 due to their direct alignment with each other. The proximal tips 74 are positioned near the first ramp surfaces 41 of the handle engagement portion 36 for contacting the first ramp surfaces 41 upon proximal force F being asserted against the protector 57a in the manner described above. The tips 74 are relatively flat members that will contact the first ramp surfaces 41 without advancing to the second ramp surfaces 43.

Similar to the protector 57 (FIG. 4) described above, the protector 57a is also made of molded plastic as single, integral component. The sinusoidal member 72 through both its configuration and material composition is a resilient, flexible member which permits the protector 57a to function similar to the protector 57 (FIG. 4) described above.

Figure 11:
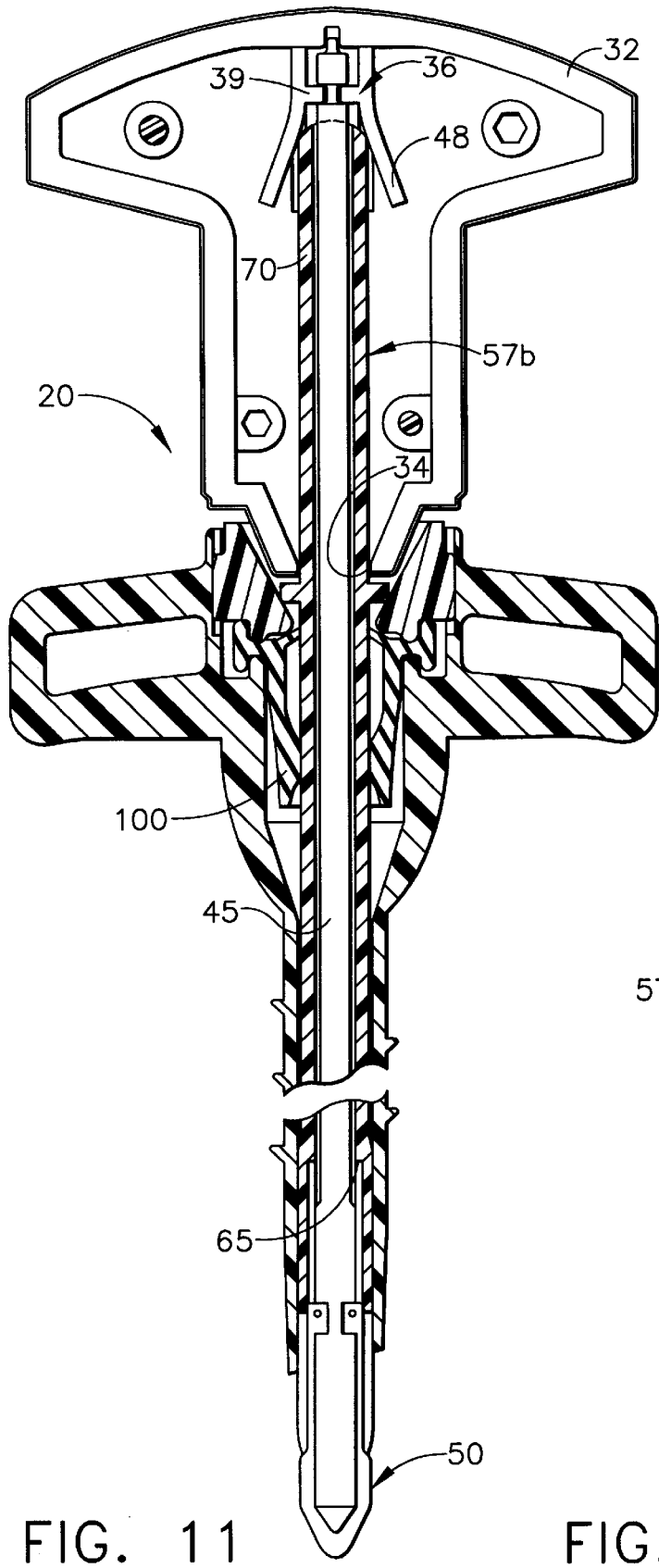
FIG. 11 is a plan view in section of an alternative embodiment of a trocar according to the present invention.

Another embodiment according to the present invention is illustrated in FIG. 11 wherein the trocar 20 includes a protector 57b having a proximal end 70. The contact portion 36 of the cannula handle 32 comprises a pair of deflectable members 48 that are movable by the proximal end 70 of the protector 57b. The deflectable members 48 are made of a flexible and resilient material such that once the proximal force F is asserted against the protector 57b, the proximal end 70 of the protector 57b is advanced proximally into the contact portion 36 slidably moving against the inner surfaces of the deflectable members 48. The protector proximal end 70 outwardly deflects the deflectable members 48 away from the obturator shaft 45 thereby retracting the protector 57b and exposing the penetrating tip 50. Accordingly, this alternative arrangement provides similar advantages to the preferred embodiment shown in FIGS. 2–5.

As mentioned above, the trocar 20 according to the present invention provides several advantages. In particular, the trocar 20 is an assembly actuated trocar and is directed to being the trocar of choice in the current cost conscious surgical environment. Since cost is a major issue with the present surgical community, it is often necessary to develop novel and creative instruments and techniques in order to provide safe, efficacious and quality surgical treatment for the patient, while at the same time seeking to reduce cost from the surgical procedure. One creative way of reducing cost from a surgical procedure afforded by the present invention, is to utilize a single fully returnable safety shielded trocar such as those described as part of the field and background of the invention, along with one or more of the trocars 20 according to the present invention.

Since a fully returnable shield trocar is more costly than the trocar 20 according to the present invention, mainly due to the cost of additional parts and manufacturing, many surgeons will seek to limit the number of fully returnable safety shielded trocars utilized during a single surgical procedure. Thus, many surgeons may opt to utilize only one fully returnable safety shielded trocar in order to establish a primary access port in the patient. The primary access port being established once the safety shielded obturator is removed from the cannula and an endoscope is inserted in its place in order to establish visualization for the placement for secondary access ports.

The secondary access ports are utilized to accommodate various types of surgical instrumentation in order to facilitate the surgical procedure. Accordingly, the trocar 20 according to the present invention can be utilized to establish these secondary access ports. As illustrated in FIG. 2, since the trocar 20 according to the present invention utilizes a protector 57, the penetrating tip 55 will be covered, and accordingly, a degree of safety is provided to all those who handle the obturator assembly 30 prior to the engagement and locking of the obturator assembly 30 into the cannula assembly 80. Additionally, the seal assembly 100 of the trocar 20 also will be protected since the penetrating tip 55 remains covered as the obturator is slid through the seal assembly 100 into the cannula sleeve 82.

Although this invention has been described in connection with its most preferred embodiments, it will become readily apparent to those reviewing this detailed specification that numerous additional embodiments fall well within the scope and spirit of the claimed invention as set forth in the claims which appear below.

What is claimed is:

1. A surgical trocar comprising:
   a cannula assembly including a sleeve having a proximal end and a passageway therethrough;
   a housing having an opening and being located at said proximal end of said sleeve, said housing opening being aligned with said passageway of said sleeve;
   an obturator assembly insertable into said cannula assembly and including a handle, an obturator shaft having a proximal end connected to said handle and a distal end opposite said proximal end, and a penetrating tip located at said distal end of said obturator shaft;
   a protector having a distal end and slidably disposed around said obturator shaft for covering said penetrating tip of said obturator shaft, said protector having an aperture at said distal end for permitting said penetrating tip of said obturator shaft to pass therethrough, said protector also having a flexible proximal end movable against said handle, said flexible proximal end being made of a resilient, flexible material, and wherein said protector being a single, integral component, said protector being movable to a retracted position in order to expose said penetrating tip past said protector aperture and said sleeve distal end when said handle contacts said housing upon an insertion of said obturator assembly into said cannula assembly wherein a proximal force is asserted against said protector, said material of said flexible proximal end causing said protector to return to a protected position thereby covering said penetrating tip upon a release of said proximal force from said protector; and a seal assembly having a S-shaped configuration located in said housing, said seal assembly having an aperture therethrough and at least one side wall having an inner surface and at least one rib on said inner surface of said at least one side wall, said rib providing stiffening to said side wall for resisting inversion of said side wall of said seal assembly upon a withdrawal of said surgical instrument from said assembly.

2. The surgical trocar according to claim 1, wherein said seal assembly includes a pair of side walls having an inner surface and at least one rib on at least one of said inner surfaces of said sidewalls.

3. The surgical trocar according to claim 2, wherein said seal assembly includes at least one rib on said inner surface of each side wall.

4. The surgical trocar according to claim 3, wherein said seal assembly further includes a diaphragm seal having a substantially convex configuration, said diaphragm seal having said aperture arranged therein.

5. The surgical trocar according to claim 4, wherein said flexible proximal end of said protector includes at least one deflectable arm slidably movable against a contact portion of said handle.

6. The surgical trocar according to claim 5, wherein said flexible proximal end of said protector includes a pair of deflectable arms slidably movable against said contact portion of said handle.

7. The surgical trocar according to claim 6, wherein said contact portion includes a first ramp surface and each deflectable arm includes an end surface at a proximal end of each arm for slidably moving against said first ramp surface of said contact portion.

8. The surgical trocar according to claim 7, wherein said contact portion further includes a second ramp surface adjacent said first ramp surface and each deflectable arm includes an inner surface adjacent said end surface for slidably moving against said second ramp surface.

9. The surgical trocar according to claim 8, wherein said protector includes a boss for contacting said handle when said protector is retracted to said retracted position.

10. The surgical trocar according to claim 9, wherein said housing includes at least one slot and said handle includes at least one pin detachably engagable with said at least one slot for locking said handle to said housing.

11. The surgical trocar according to claim 10, wherein said penetrating tip includes a flat blade.

12. The surgical trocar according to claim 11, wherein said protector includes a dilation section at said distal end of said protector.

13. The surgical trocar according to claim 12, wherein said sleeve includes a helical thread on an exterior surface of said sleeve.

14. The surgical trocar according to claim 1, wherein said flexible proximal end of said protector includes a sinusoidal member for contacting a contact portion of said handle.

15. The surgical trocar according to claim 14, wherein said sinusoidal member includes a pair of tips and a notch interposed therebetween at a proximal end of said sinusoidal member.

16. The surgical trocar according to claim 15, wherein said sinusoidal member also includes a central opening therethrough, said central opening and said notch shaped to receive said obturator shaft.

17. The surgical trocar according to claim 16, wherein said protector includes a boss for contacting said handle when said protector is retracted to said retracted position.

18. The surgical trocar according to claim 17, wherein said housing includes at least one slot and said handle includes at least one pin detachably engagable with said at least one slot for locking said handle to said housing.

19. The surgical trocar according to claim 18, wherein said penetrating tip includes a flat blade.

20. The surgical trocar according to claim 19, wherein said protector includes a dilation section at said distal end of said protector.

21. The surgical trocar according to claim 20, wherein said sleeve includes a helical thread on an exterior surface of said sleeve.

* * * * *